(12) United States Patent
Choi et al.

(10) Patent No.: US 8,053,605 B2
(45) Date of Patent: Nov. 8, 2011

(54) PHOSPHORUS-CONTAINING CATALYST COMPOSITION AND HYDROFORMYLATION PROCESS USING THE SAME

(75) Inventors: Jae-Hui Choi, Daejeon (KR); Dong-Hyun Ko, Daejeon (KR); Sung-Shik Eom, Daejeon (KR); Sang-Gi Lee, Daejeon (KR); Moo-Ho Hong, Daejeon (KR); O-Hark Kwon, Daejeon (KR)

(73) Assignee: LG Chem, Ltd., Seoul (KR)

( * ) Notice: Subject to any disclaimer, the term of this patent is extended or adjusted under 35 U.S.C. 154(b) by 94 days.

(21) Appl. No.: 12/677,496

(22) PCT Filed: Jun. 5, 2008

(86) PCT No.: PCT/KR2008/003159
§ 371 (c)(1),
(2), (4) Date: Mar. 10, 2010

(87) PCT Pub. No.: WO2009/035204
PCT Pub. Date: Mar. 19, 2009

(65) Prior Publication Data
US 2010/0324339 A1    Dec. 23, 2010

(30) Foreign Application Priority Data

Sep. 14, 2007 (KR) .......... 10-2007-0093716

(51) Int. Cl.
*C07C 45/50* (2006.01)
*B01J 31/12* (2006.01)

(52) U.S. Cl. ......... 568/454; 502/155
(58) Field of Classification Search .......... 568/454; 502/155

See application file for complete search history.

(56) References Cited

U.S. PATENT DOCUMENTS

| | | |
|---|---|---|
| 6,486,359 B1 | 11/2002 | Maas et al. |
| 7,173,138 B2 | 2/2007 | Ahlers et al. |

FOREIGN PATENT DOCUMENTS

| | | |
|---|---|---|
| JP | 2-174740 | 7/1990 |
| JP | 4-339809 | 11/1992 |
| KR | 10-2001-0109732 A | 12/2001 |
| KR | 10-2005-0118023 A | 12/2005 |
| KR | 10-0547587 | 1/2006 |
| WO | WO 99/13984 A1 | 3/1999 |
| WO | WO 2005/120704 | 12/2005 |

*Primary Examiner* — Sikarl Witherspoon
(74) *Attorney, Agent, or Firm* — McKenna Long & Aldridge LLP

(57) ABSTRACT

The present invention relates to a catalyst composition that includes a triphenylphosphine ligand, a monodentate phosphine ligand, a monodentate phosphine oxide ligand, and a transition metal catalyst, and a hydroformylation process using the same. In the hydroformylation process using the catalyst composition according to the present invention, the high catalytic activity can be obtained, and the selectivity (N/I selectivity) in respects to normal- or iso-aldehyde can be desirably controlled.

19 Claims, No Drawings

US 8,053,605 B2

PHOSPHORUS-CONTAINING CATALYST COMPOSITION AND HYDROFORMYLATION PROCESS USING THE SAME

This application claims the benefit of PCT/KR2008/003159 filed on Jun. 5, 2008 and Korean Patent Application No. 10-2007-0093716 filed on Sep. 14, 2007, both of which are hereby incorporated herein by reference for all purposes in their entirety.

TECHNICAL FIELD

The present invention relates to a phosphorus-containing catalyst composition and a hydroformylation process using the same, and more particularly, to a catalyst composition that includes a triphenylphosphine compound, a monodentate phosphine compound, a monodentate phosphine oxide compound, and a transition metal catalyst, and a hydroformylation process using the same.

BACKGROUND ART

A hydroformylation reaction in which an olefin reacts with a synthesis gas ($CO/H_2$) in the presence of a homogeneous organicmetallic catalyst and a ligand to produce linear (normal) and branched (iso) aldehyde which has one more carbon atom than olefin was originally discovered by Otto Roelen in Germany in 1938.

In general, the hydroformylation that is known as an oxo reaction is a very important industrial reaction in views of a homogeneous system catalyst reaction, and currently, about 9,600,000 tons of aldehydes (including alcohol derivatives) are produced by the oxo process and consumed all over the world (SRI report, September 2006, 682. 7000 page 7).

Various types of aldehydes produced by the oxo reaction are oxidized to carboxylic acids or hydrogenated to alcohols. In addition, aldehydes can also be converted to long alkyl chain-containing acids or alcohols through aldol condensation and then oxidation or reduction. In particular, hydrogenated alcohol of aldehyde, which is obtained by the oxo reaction, is called oxo alcohol. Oxo alcohol is industrially extensively used as a solvent, an additive, various types of raw materials of plasticizers, synthesis lubricants, and chemical intermediates.

It is known that a metal carbonyl hydride compound has a catalytic activity of the hydroformylation reaction. The N/I (ratio of linear (normal) to branched (iso) isomers) selectivity of aldehydes varies according to the type of ligand used and operating conditions.

Modern hydroformylation research is almost exclusively focused on cobalt(Co), rhodium(Rh), platinum(Pt) and ruthenium(Ru) metal catalyst. In respects to the transition metals, it is known that the order of the catalytic activity is Rh>>Co>Ir, Ru>Os>Pt>Pd>Fe>Ni. Platinum and ruthenium catalyst are mainly subjects of academic interest. Therefore, cobalt and rhodium catalysts have been mainly used in an oxo process. To date, a rhodium-based low-pressure oxo process (LPO Process) has been adopted in at least 70% of oxo plants worldwide because of the high efficiency, high yield of normal products, and mild reaction condition even though there are disadvantages of the expensive catalyst and catalytic deactivation due to the poisoning.

Examples of the ligand that is used during the oxo process include phosphine ($PR_3$, $R=C_6H_5$, and $n-C_4H_9$), phosphine oxide, and phosphite. In the case of when rhodium is used as the central metal, it is known that the ligand having the catalytic activity and the stability that are better than those of triphenylphosphine (TPP) is almost not present. Thus, in most oxo process, Rh metal is used as a catalyst and TPP is used as a ligand. In addition, to increase the stability of a catalytic system, TPP ligand is used in an amount of at least 100 equivalent of the catalyst.

In general, since the value of the linear aldehyde derivative is high among aldehydes that are products of the oxo reaction, many studies have been made to increase the ratio of the linear aldehyde in respects to the catalyst. However, recently, products obtained by using iso-aldehyde as the raw materials instead of the linear aldehyde, for example, an isobutyric acid, neopentyl glycol (NPG), 2,2,4-trimethyl-1,3-pentanediol, an isovaleric acid and the like have been developed, thus the use of iso-aldehyde has been increased. Accordingly, there is a demand to develop a technology of producing normal- and iso-aldehyde required in a market by desirably controlling the N/I selectivity while the excellent catalytic activity is maintained.

DISCLOSURE OF INVENTION

Technical Problem

Therefore, the present invention has been made keeping in mind the above problems occurring in the related art, and it is an object of the present invention to provide a catalyst composition that has excellent catalytic activity and stability and is capable of controlling normal/iso (N/I) selectivity of generated aldehyde, and a hydroformylation process using the same.

Technical Solution

The inventors of the present invention have found that if a triphenylphosphine ligand, a monodentate phosphine ligand, and a monodentate phosphine oxide ligand are applied to a hydroformylation reaction of olefin at the same time, the catalytic activity and the stability are excellent and the N/I selectivity can be controlled.

Advantageous Effects

According to the catalyst composition of the present invention and the hydroformylation process using the same, the monodentate phosphine and the monodentate phosphine oxide ligand are applied to the hydroformylation reaction of olefin in conjunction with triphenylphosphine to control the N/I selectivity while the high catalytic activity is maintained.

In addition, the ligands are continuously consumed during an aldehyde recovering process of a continuous hydroformylation process. Accordingly, a desirable ligand is selected in consideration of the desired N/I selectivity and injected into the reactor. Thus, it is easy to apply the above ligands in practice.

BEST MODE FOR CARRYING OUT THE INVENTION

Accordingly, the present invention provides a catalyst composition that includes a triphenylphosphine ligand that is represented by the following Formula 1; a monodentate phosphine ligand that is represented by the following Formula 2; a monodentate phosphine oxide ligand that is represented by the following Formula 3; and a transition metal catalyst that is represented by the following Formula 4.

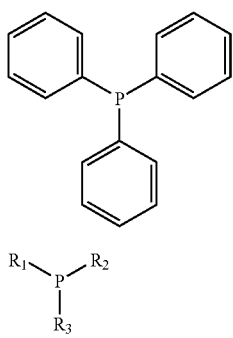

[Formula 1]

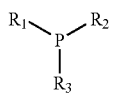

[Formula 2]

In the above Formula 2, $R_1$, $R_2$, and $R_3$ are each independently a substituted or unsubstituted alkyl group having 1 to 20 carbon atoms; a substituted or unsubstituted cycloalkyl group or cycloalkenyl group having 5 to 20 carbon atoms; a substituted or unsubstituted aryl group having 6 to 36 carbon atoms; a substituted or unsubstituted heteroalkyl group having 1 to 20 carbon atoms; a substituted or unsubstituted heteroaryl group having 4 to 36 carbon atoms; or a substituted or unsubstituted hetero ring group having 4 to 36 carbon atoms, the hetero alkyl group, the hetero aryl group, and the hetero ring group include one or more atoms that are selected from the group consisting of N, O, and S, and a substituent group is nitro(—$NO_2$), fluorine(F), chlorine (Cl), bromine(Br), or an alkyl group having 1 to 4 carbon atoms when $R_1$, $R_2$, and $R_3$ are substituted by the substituent group, with a proviso that $R_1$, $R_2$, and $R_3$ are not an unsubstituted phenyl group at the same time.

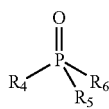

[Formula 3]

In the above Formula 3, $R_4$, $R_5$, and $R_6$ are each independently a substituted or unsubstituted alkyl group having 1 to 20 carbon atoms; a substituted or unsubstituted cycloalkyl group or cycloalkenyl group having 5 to 20 carbon atoms; a substituted or unsubstituted aryl group having 6 to 36 carbon atoms; a substituted or unsubstituted heteroalkyl group having 1 to 20 carbon atoms; a substituted or unsubstituted heteroaryl group having 4 to 36 carbon atoms; or a substituted or unsubstituted hetero ring group having 4 to 36 carbon atoms, the hetero alkyl group, the hetero aryl group, and the hetero ring group include one or more atoms that are selected from the group consisting of N, O, and S, and a substituent group is nitro(—$NO_2$), fluorine(F), chlorine (Cl), bromine(Br), or an alkyl group having 1 to 4 carbon atoms when $R_4$, $R_5$, and $R_6$ are substituted by the substituent group.

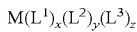

[Formula 4]

In the above Formula 4, M is a transition metal, preferably any one selected from cobalt(Co), rhodium(Rh), and iridium (Ir), and more preferably rhodium(Rh), $L^1$, $L^2$, and $L^3$ are each independently selected from the group consisting of hydrogen, CO, cyclooctadiene, norbornene, chlorine, triphenylphosphine, and acetylacetonato, x, y, and z are each independently 0 to 5, and x, y, and z are not 0 at the same time.

Preferably, in respects to the transition metal catalyst that is represented by the above Formula 4, there are cases of when $L^1$ is CO, $L^2$ is acetylacetonato, and x and y are 2 and 1, respectively (z is 0), when $L^1$ is CO, $L^2$ is acetylacetonato, $L^3$ is triphenylphosphine, and x, y, and z are all 1, and when $L^1$ is CO, $L^2$ is hydrogen, $L^3$ is triphenylphosphine, x, y, and z are each independently 1, 1, and 3.

In addition, the present invention provides a hydroformylation process of an olefin-based compound, which includes a) dissolving a triphenylphosphine ligand that is represented by the following Formula 1, a monodentate phosphine ligand that is represented by the following Formula 2, a monodentate phosphine oxide ligand that is represented by the following Formula 3, and a transition metal catalyst that is represented by the following Formula 4 in a solvent to produce a catalyst composition; and b) reacting the olefin-based compound, and a synthesis gas (carbon monoxide and hydrogen) in the presence of the catalyst composition to produce aldehyde.

In the case of when the olefin compound and the synthesis gas (carbon monoxide and hydrogen) are reacted with each other, it is preferable to produce aldehyde by performing the heating and the pressurizing while the agitation is conducted.

It is preferable that the monodentate phosphine ligand represented by the above Formula 2 be one or more selected from the group consisting of trim-tolylphosphine(TMTP), diphenyl(p-tolyl)phosphine(DPPTP), tris(2,6-dimethoxyphenyl)phosphine(TDMPP), tris(4-methoxyphenyl)phosphine (TMPP), trimesitylphosphine(TMSTP), tris-3,5-xylylphosphine(TXP), tricyclohexylphosphine(TCHP), tribenzylphosphine(TBP), benzyl diphenylphosphine (BDPP), and diphenyl(2-methoxyphenyl)phosphine(DPMPP).

It is preferable that the monodentate phosphine oxide ligand represented by the above Formula 3 be one or more selected from the group consisting of trim-tolylphosphine oxide(TMTPO), diphenyl(p-tolyl)phosphine oxide (DPPTPO), tris(2,6-dimethoxyphenyl)phosphine oxide(TDMPPO), tris(4-methoxyphenyl)phosphine oxide(TMPPO), trimesitylphosphine oxide(TMSTPO), tris-3,5-xylylphosphine oxide(TXPO), tricyclohexylphosphine oxide (TCHPO), tribenzylphosphine oxide(TBPO), benzyl diphenylphosphine oxide(BDPPO), and diphenyl(2-methoxyphenyl)phosphine oxide(DPMPPO).

Preferably, the content of each of the triphenylphosphine ligand, the monodentate phosphine ligand, and the monodentate phosphine oxide ligand is in the range of 0.5 to 150 mole based on 1 mole of the above transition metal catalyst. More preferably, the content is in the range of 10 to 100 mole. It is preferable that the total content of the triphenylphosphine ligand, the monodentate phosphine ligand, and the monodentate phosphine oxide ligand be in the range of 100 to 200 mole based on 1 mole of the transition metal catalyst. In connection with this, if the total content of the above ligands is less than 100 mole based on 1 mole of the transition metal catalyst, there is a problem in stability of the catalyst system. If the total content of the above ligands is more than 200 mole, since an excessive amount of the costly ligand is used without an additional benefit, there is a problem in that cost is increased.

The above transition metal catalyst may include one or more compounds selected from the group consisting of cobalt carbonyl($CO_2(CO)_8$), acetylacetonato dicarbonyl rhodium (Rh(AcAc)(CO)$_2$), acetylacetonato carbonyltriphenylphosphine rhodium(Rh(AcAc)(CO)(TPP)), hydrido carbonyltri (triphenylphosphine) rhodium(HRh(CO)(TPP)$_3$), acetylacetonato dicarbonyl iridium(Ir(AcAc)(CO)$_2$), and hydrido carbonyl tri(triphenylphosphine) iridium(HIr(CO)(TPP)$_3$). In connection with this, it is preferable that the above transition metal catalyst be acetylacetonato carbonyltriphenylphosphine rhodium(Rh(AcAc)(CO)(TPP), ROPAC).

Preferably, in respects to the content of the above transition metal catalyst, the content of free metal is in the range of 10 to 1000 ppm based on a weight or a volume of the catalyst composition. More preferably, the content is in the range of 50 to 500 ppm. In the case of when the content of the transition metal is less than 10 ppm, since the reaction rate of the hydroformylation is slow, it is undesirable in practice. In the case of when the content of the transition metal is more than 1000 ppm, since the transition metal is costly, the cost is increased and the excellent effect is not obtained in terms of the reaction rate.

In the above hydroformylation process, it is preferable that the above olefin-based compound be a compound that is represented by the following Formula 5.

[Formula 5]

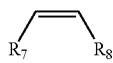

In the above Formula 5, $R_7$ and $R_8$ are each independently any one selected from the group consisting of hydrogen, an alkyl group having 1 to 20 carbon atoms, a fluorine group(—F), a chlorine group(—Cl), a bromine group(—Br), a trifluoromethyl group(—$CF_3$), and an aryl group having 0 to 5 substituent groups and 6 to 20 carbon atoms, and the substituent group of the aryl group may be selected from the group consisting of nitro(—$NO_2$), fluorine(—F), chlorine(—Cl), bromine(—Br), a methyl group, an ethyl group, a propyle group, and a butyl group.

In the case of when $R_7$ or $R_8$ is the aryl group, it is preferable that the aryl group be a phenyl group.

Specifically, the olefin-based compound may be one or more compounds selected from the group consisting of ethene, propene, 1-butene, 1-pentene, 1-hexene, 1-octene, and styrene.

In the above hydroformylation process, examples of the above solvent may include one or more compounds selected from the group consisting of aldehydes including propionaldehyde, butyraldehyde, pentylaldehyde, and valeraldehyde; ketones including acetone, methyl ethyl ketone, methyl isobutyl ketone, acetophenone, and cyclohexanone; alcohols including ethanol, pentanol, octanol, and texanol; aromatics including benzene, toluene, and xylene; halogenated aromatics including orthodichlorobenzene; ethers including tetrahydrofuran, dimethoxyethane, and dioxane; halogenated paraffins including methylene chloride; and paraffin hydrocarbons including heptane, and preferably, various types of aldehydes and aromatics such as toluene.

In the above hydroformylation process, the composition ratio of CO:$H_2$ that are the synthesis gas may vary, preferably be in the range of about 5:95 to 70:30, more preferably about 40:60 to 60:40, and most preferably about 50:50 to 40:60.

In the hydroformylation process, the preferable reaction temperature and reaction pressure may include those known in the art. For example, in the above hydro-formylation process, the hydroformylation process is performed at the reaction temperature in the range of preferably about 20 to 180° C., more preferably about 50 to 150° C., and most preferably about 75 to 105° C.

In the above hydroformylation process, the hydroformylation process is performed at the reaction pressure in the range of preferably about 1 to 700 bar, more preferably about 1 to 300 bar, and most preferably about 5 to 30 bar.

The reaction caused by the above hydroformylation process may be shown in the following Reaction Equation 1.

[Reaction Equation 1]

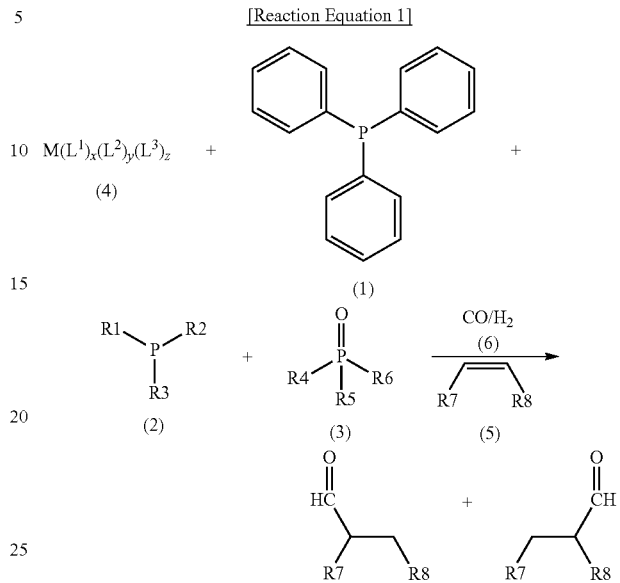

In order to perform the above hydroformylation reaction, first, the transition metal catalyst 4, and the ligands 1, 2, and 3 are dissolved in a solvent such as benzene, toluene, ethanol, pentanol, octanol, texanol, butyraldehyde, and pentylaldehyde to prepare a solution mixture of the catalyst and the ligands.

The olefin compound 5, and the synthesis gas 6 of carbon monoxide and hydrogen are injected in conjunction with the solution mixture of the catalyst and the ligands into the reactor, agitated, heated and pressurized to perform the hydroformylation reaction.

The ligands are continuously consumed during an aldehyde recovering process of a continuous hydroformylation process. Accordingly, a desirable ligand is selected in consideration of the desired N/I selectivity and injected into the reactor. Thus, it is easy to apply the above ligands in practice.

MODE FOR THE INVENTION

Hereinafter, the present invention will be described in detail in light of Examples. The present invention may, however, be embodied in many different forms and should not be construed as being limited to the Examples set forth herein. Rather, these Examples are provided such that this disclosure will be thorough and complete and will fully convey the concept of the present invention to those skilled in the art.

Examples 1 to 11

The hydroformylation reaction of propene using the acetylacetonato carbonyltriphenylphosphine rhodium (Rh(AcAc)(CO)(TPP), ROPAC) catalyst, the triphenylphosphine compound, the monodentate phosphine compound, and the monodentate phosphine oxide compound 0.010 mg of ROPAC (0.390 mmol) that was the catalyst, TPP that was the triphenyl phosphine compound L1, TMTP, BDPP, TCHP, TBP, DPMPP, TMSTP, DPPTP, or TDMPP that was the monodentate phosphine compound L2, and TMTPO, BDPPO, TCHPO, DPMPPO, TMSTPO, DPPTPO, or TDMPPO that was the monodentate phosphine oxide compound L3 were dissolved in the toluene solvent according to the molar ratio (L/Rh) of the ligand to metal (Rh) of ROPAC described in Table 1 in the autoclave reactor having the volume of 20 ml so that the total volume of the solution was 10 ml, and then added. Propene (olefin):CO:$H_2$ were injected into the above reaction solution, and the reaction was performed for 2.5 hours while the pressure in the reactor was maintained at 8 bar and the agitation was performed at 85° C.

The types of the catalyst and the ligand to the above reaction, the molar ratio of the ligand to the catalyst, the N/I selectivity, and the catalytic activity are described in Table 1 in detail.

In Examples and Comparative Examples of the present invention, the N/I selectivity was the value that was obtained by dividing the amount of normal-butyraldehyde by the amount of iso-butyraldehyde, and the amount of generated aldehyde was obtained by performing the gas chromatography (GC) analysis based on the amount of hexadecane that was added as the internal standard substance.

The catalytic activity was the value that was obtained by dividing the total amount of normal-aldehyde and iso-aldehyde generated during the above reaction by the molecular weight of butyraldehyde, the concentration of the used catalyst, and the reaction time. In connection with this, the unit of the catalytic activity was mol(BAL)/mol(Rh)/h.

Comparative Examples 1 to 3

The hydroformylation reaction of propene using the acetylacetonato carbonyltriphenylphosphine rhodium (Rh(AcAc)(CO)(TPP), ROPAC) catalyst, the triphenylphosphine compound, diphenylcyclohexylphosphine(DPCHP), and tris(p-tolyl)phosphine(TPTP)

TPP (Comparative Example 1), TPP and DPCHP (Comparative Example 2), and TPP and TPTP (Comparative Example 3) that were the triphenylphosphine compound were used as the ligand to perform the catalytic activity test by using the same method as Examples 1 to 11 according to the molar ratio described in the following Table 1, and the results are described in the following Table 1.

TABLE 1

| Comparison | Catalyst | L1 | L2 | L3 | L1/Rh mol/mol | L2/Rh mol/mol | L3/Rh mol/mol | N/I | Catalytic activity (mol$_{BAL}$/mol$_{(Rh)}$/h) |
|---|---|---|---|---|---|---|---|---|---|
| Example 1 | ROPAC | TPP | TMTP | TMTPO | 60 | 20 | 20 | 6.4 | 152.3 |
| Example 2 | ROPAC | TPP | TMTP | TCHPO | 60 | 20 | 20 | 5.5 | 147.5 |
| Example 3 | ROPAC | TPP | BDPP | BDPPO | 60 | 20 | 20 | 4.7 | 148.1 |
| Example 4 | ROPAC | TPP | BDPP | TCHPO | 60 | 20 | 20 | 4.0 | 145.7 |
| Example 5 | ROPAC | TPP | TCHP | TCHPO | 60 | 10 | 30 | 2.7 | 133.3 |
| Example 6 | ROPAC | TPP | TBP | BDPPO | 60 | 10 | 30 | 3.5 | 143.6 |
| Example 7 | ROPAC | TPP | DPMPP | DPMPPO | 60 | 30 | 10 | 14.7 | 147.7 |
| Example 8 | ROPAC | TPP | DPMPP | TMSTPO | 60 | 30 | 10 | 13.9 | 153.4 |
| Example 9 | ROPAC | TPP | TMSTP | TMSTPO | 60 | 20 | 20 | 11.6 | 161.2 |
| Example 10 | ROPAC | TPP | DPPTP | DPPTPO | 60 | 30 | 10 | 11.9 | 137.9 |
| Example 11 | ROPAC | TPP | TDMPP | TDMPPO | 50 | 40 | 10 | 14.8 | 154.6 |
| Comparative Example 1 | ROPAC | TPP | — | — | 100 | — | — | 9.9 | 131.3 |
| Comparative Example 2 | ROPAC | TPP | DPCHP | — | 60 | 40 | — | 5.8 | 104.8 |
| Comparative Example 3 | ROPAC | TPP | TPTP | — | 60 | 40 | — | 8.9 | 117.9 |

L1: triphenyl phosphine compound,
L2: mono-coordinated phosphine compound,
L3: mono-coordinated phosphine oxide compound

Examples 12 to 14

Stability test of the catalyst composition including the acetylacetonato carbonyltriphenylphosphine rhodium (Rh(AcAc)(CO)(TPP), ROPAC) catalyst, the triphenylphosphine compound, the monodentate phosphine compound, and the monodentate phosphine oxide compound 0.150 mg of ROPAC that was the catalyst (0.390 mmol), 0.3 ml of hexadecane that was the internal standard substance for GC analysis, TPP that was the triphenyl phosphine compound (L1), TMTP, TCHP or TMSTP that was the monodentate phosphine compound (L2), and TCHPO or TMSTPO that was the monodentate phosphine oxide compound were dissolved in the toluene solvent according to the molar ratio (L/Rh) of the ligand to metal (Rh) of ROPAC that was described in the following Table 2 in the autoclave reactor having the volume of 300 ml so that the total volume of the resulting solution was 150 ml, and then added. The gas in which the molar ratio of CO:$H_2$ was 1:1 was injected into the above solution to perform the aging test while the pressure in the reactor was maintained at 6 bar and the agitation was performed at 105° C. About 30 ml of the solution was sampled according to the time described in Table 2 and the test of the catalytic activity was performed by using the same method as Examples 1 to 11. The catalytic activities obtained from the conditions are described in Table 2, and the catalytic activity under each condition is a relative value when the catalytic activity of the fresh catalyst solution that is not subjected to the aging test is considered to be 100.

Comparative Example 4

Stability test of the catalyst composition including the acetylacetonato carbonyltriphenylphosphine rhodium (Rh(AcAc)(CO)(TPP), ROPAC) catalyst and the triphenylphosphine compound The catalyst composition was prepared by using the same method as Examples 12 to 14, except that TPP was used as the ligand. Next, the aging test and the catalytic activity test were performed. The results are described in the following Table 2.

TABLE 2

| Comparison | Catalyst | L1 | L2 | L3 | L1/Rh mol/mol | L2/Rh mol/mol | L3/Rh mol/mol | Catalytic activity (%) | | | |
|---|---|---|---|---|---|---|---|---|---|---|---|
| | | | | | | | | Fresh | 5 hr | 25 hr | 50 hr |
| Example 12 | ROPAC | TPP | TMTP | TCHPO | 60 | 20 | 20 | 100 | 49 | 43 | 26 |
| Example 13 | ROPAC | TPP | TCHP | TCHPO | 60 | 10 | 30 | 100 | 48 | 44 | 31 |
| Example 14 | ROPAC | TPP | TMSTP | TMSTPO | 60 | 20 | 20 | 100 | 43 | 40 | 23 |
| Comparative Example 4 | ROPAC | TPP | — | — | 100 | — | — | 100 | 44 | 39 | 24 |

L1: triphenyl phosphine compound,
L2: mono-coordinated phosphine compound,
L3: mono-coordinated phosphine oxide compound With reference to the above Examples and Comparative Examples, the catalytic activity is excellent as compared to the case of when the triphenylphosphine ligand, the monodentate phosphine ligand, and the monodentate phosphine oxide ligand are mixed with each other at the same time, the case of when only triphenylphosphine (TPP) is used as the ligand under the same condition, the case of when TPP and DPCHP are used at the same time, and the case of when TPP and TPTP are used at the same time. In addition, it can be seen that the N/I selectivity can be controlled to be in the range of 2 to 15 by the selection of the desirable ligand, and the composition can be used during an oxo process in practice because the stability of the composition is almost similar to that of triphenylphosphine.

The invention claimed is:

1. A catalyst composition for hydroformylation reaction of an olefin-based compound comprising: a triphenylphosphine ligand that is represented by the following Formula 1; a monodentate phosphine ligand that is represented by the following Formula 2; and a monodentate phosphine oxide ligand that is represented by the following Formula 3; and a transition metal catalyst is one or more selected from the group consisting of cobalt carbonyl($Co_2(CO)_8$), acetylacetonato dicarbonyl rhodium($Rh(AcAc)(CO)_2$), acetylacetonato carbonyltriphenylphosphine rhodium($Rh(AcAc)(CO)(TPP)$), hydrido carbonyltri(triphenylphosphine)rhodium($HRh(CO)(TPP)_3$), acetylacetonato dicarbonyl iridium($Ir(AcAc)(CO)_2$), and hydrido carbonyltri(triphenylphosphine) iridium($HIr(CO)(TPP)_3$):

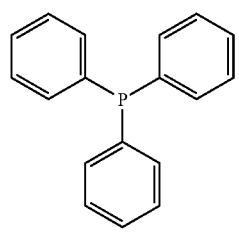

[Formula 1]

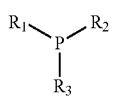

[Formula 2]

wherein $R_1$, $R_2$, and $R_3$ are each independently a substituted or unsubstituted alkyl group having 1 to 20 carbon atoms; a substituted or unsubstituted cycloalkyl group or cycloalkenyl group having 5 to 20 carbon atoms; a substituted or unsubstituted aryl group having 6 to 36 carbon atoms; a substituted or unsubstituted heteroalkyl group having 1 to 20 carbon atoms; a substituted or unsubstituted heteroaryl group having 4 to 36 carbon atoms; or a substituted or unsubstituted hetero ring group having 4 to 36 carbon atoms, the hetero alkyl group, the hetero aryl group, and the hetero ring group include one or more atoms that are selected from the group consisting of N, O, and S, when $R_1$, $R_2$, and $R_3$ are substituted by the substituent group, the substituent group is nitro(—$NO_2$), fluorine (F), chlorine(Cl), bromine(Br), or an alkyl group having 1 to 4 carbon atoms, with a proviso that $R_1$, $R_2$, and $R_3$ are not an unsubstituted phenyl group at the same time,

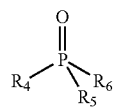

[Formula 3]

wherein $R_4$, $R_5$, and $R_6$ are each independently a substituted or unsubstituted alkyl group having 1 to 20 carbon atoms; a substituted or unsubstituted cycloalkyl group or cycloalkenyl group having 5 to 20 carbon atoms; a substituted or unsubstituted aryl group having 6 to 36 carbon atoms; a substituted or unsubstituted heteroalkyl group having 1 to 20 carbon atoms; a substituted or unsubstituted heteroaryl group having 4 to 36 carbon atoms; or a substituted or unsubstituted hetero ring group having 4 to 36 carbon atoms, the hetero alkyl group, the hetero aryl group, and the hetero ring group include one or more atoms that are selected from the group consisting of N, O, and S, when $R_4$, $R_5$, and $R_6$ are substituted by the substituent group, the substituent group is nitro(—$NO_2$), fluorine (F), chlorine(Cl), bromine(Br), or an alkyl group having 1 to 4 carbon atoms.

2. The catalyst composition for hydroformylation reaction of an olefin-based compound as set forth in claim 1, wherein a content of free metal of the transition metal catalyst is in the range of 10 to 1000 ppm based on a weight of the catalyst composition.

3. The catalyst composition for hydroformylation reaction of an olefin-based compound as set forth in claim 1, wherein a content of each of the triphenylphosphine ligand, the monodentate phosphine ligand, and the monodentate phosphine oxide ligand is in the range of 0.5 to 150 mole based on 1 mole of the transition metal catalyst.

4. The catalyst composition for hydroformylation reaction of an olefin-based compound as set forth in claim 1, wherein a total content of the triphenylphosphine ligand, the monodentate phosphine ligand, and the monodentate phosphine oxide ligand is in the range of 100 to 200 mole based on 1 mole of the transition metal catalyst.

5. The catalyst composition for hydroformylation reaction of an olefin-based compound as set forth in claim 1, wherein the monodentate phosphine ligand is one or more selected from the group consisting of tri-m-tolylphosphine(TMTP), diphenyl(p-tolyl)phosphine(DPPTP), tris(2,6-dimethoxyphenyl)phosphine(TDMPP), tris(4-methoxyphenyl)phosphine(TMPP), trimesitylphosphine(TMSTP), tris-3,5-xylylphosphine(TXP), tricyclohexylphosphine(TCHP), tribenzylphosphine(TBP), benzyl diphenylphosphine (BDPP), and diphenyl-n-propylphosphine(DPMPP).

6. The catalyst composition for hydroformylation reaction of an olefin-based compound as set forth in claim 1, wherein the monodentate phosphine oxide ligand is one or more selected from the group consisting of tri-m-tolylphosphine oxide(TMTIO), diphenyl(p-tolyl)phosphine oxide (DPPTPO), tris(2,6-dimethoxyphenyl)phosphine oxide(TDMPPO), tris(4-methoxyphenyl)phosphine oxide (TMPPO), trimesitylphosphine oxide(TMSTPO), tris-3,5-xylylphosphine oxide(TXPO), tricyclohexylphosphine oxide (TCHPO), tribenzylphosphine oxide(TBPO), benzyl diphenylphosphine oxide(BDPPO), and diphenyl-n-propylphosphine oxide(DPMPPO).

7. The catalyst composition for hydroformylation reaction of an olefin-based compound as set forth in claim 1, wherein the catalyst composition further includes a solvent, and the solvent is one or more compounds selected from the group consisting of propanaldehyde, butylaldehyde, pentylaldehyde, valeraldehyde, acetone, methyl ethyl ketone, methyl isobutyl ketone, acetophenone, cyclohexanone, ethanol, pentanol, octanol, texanol, benzene, toluene, xylene, orthodichlorobenzene, tetrahydrofuran, dimethoxyethane, dioxane, methylene chloride and heptane.

8. A hydroformylation process of an olefin-based compound, the hydroformylation process comprising:
a) dissolving a triphenylphosphine ligand that is represented by the following Formula 1, a monodentate phosphine ligand that is represented by the following Formula 2, a monodentate phosphine oxide ligand that is represented by the following Formula 3, and a transition metal catalyst which is one or more selected from the group consisting of cobalt carbonyl($Co_2(CO)_8$), acetylacetonato dicarbonyl rhodium(Rh(AcAc)(CO)$_2$), acetylacetonato carbonyltriphenylphosphine rhodium (Rh(AcAc)(CO)(TPP)), hydrido) carbonyltri(triphenylphosphine)rhodium (HRh(CO)(TPP)$_3$), acetylacetonato dicarbonyl iridium(Ir(AcAc)(CO)$_2$), and hydrido carbonyl tri(triphenylphosphine) iridium(HIr(CO)(TPP)$_3$); and
b) reacting the olefin-based compound, and a synthesis gas of carbon monoxide and hydrogen in the presence of the catalyst composition to produce aldehyde:

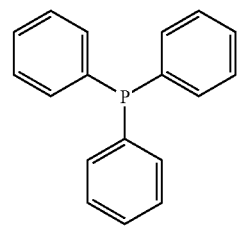

[Formula 1]

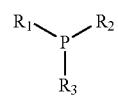

[Formula 2]

wherein $R_1$, $R_2$, and $R_3$ are each independently a substituted or unsubstituted alkyl group having 1 to 20 carbon atoms; a substituted or unsubstituted cycloalkyl group or cycloalkenyl group having 5 to 20 carbon atoms; a substituted or unsubstituted aryl group having 6 to 36 carbon atoms; a substituted or unsubstituted heteroalkyl group having 1 to 20 carbon atoms; a substituted or unsubstituted heteroaryl group having 4 to 36 carbon atoms; or a substituted or unsubstituted hetero ring group having 4 to 36 carbon atoms, the hetero alkyl group, the hetero aryl group, and the hetero ring group include one or more atoms that are selected from the group consisting of N, O, and S, when $R_1$, $R_2$, and $R_3$ are substituted by the substituent group, the substituent group is nitro(—$NO_2$), fluorine (F), chlorine(Cl), bromine(Br), or an alkyl group having 1 to 4 carbon atoms, with a proviso that $R_1$, $R_2$, and $R_3$ are not an unsubstituted phenyl group at the same time,

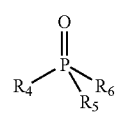

[Formula 3]

wherein $R_4$, $R_5$, and $R_6$ are each independently a substituted or unsubstituted alkyl group having 1 to 20 carbon atoms; a substituted or unsubstituted cycloalkyl group or cycloalkenyl group having 5 to 20 carbon atoms; a substituted or unsubstituted aryl group having 6 to 36 carbon atoms; a substituted or unsubstituted heteroalkyl group having 1 to 20 carbon atoms; a substituted or unsubstituted heteroaryl group having 4 to 36 carbon atoms; or a substituted or unsubstituted hetero ring group having 4 to 36 carbon atoms, the hetero alkyl group, the hetero aryl group, and the hetero ring group include one or more atoms that are selected from the group consisting of N, O, and S, when $R_4$, $R_5$, and $R_6$ are substituted by the substituent group, the substituent group is nitro(—$NO_2$), fluorine(F), chlorine (Cl), bromine(Br), or an alkyl group having 1 to 4 carbon atoms.

9. The hydroformylation process as set forth in claim 8, wherein a content of free metal of the transition metal catalyst is in the range of 10 to 1000 ppm based on a weight of the catalyst composition.

10. The hydroformylation process as set forth in claim 8, wherein a content of each of the triphenylphosphine ligand, the monodentate phosphine ligand, and the monodentate phosphine oxide ligand is in the range of 0.5 to 150 mole based on 1 mole of the transition metal catalyst.

11. The hydroformylation process as set forth in claim 8, wherein a total content of the triphenylphosphine ligand, the monodentate phosphine ligand, and the monodentate phosphine oxide ligand is in the range of 100 to 200 mole based on 1 mole of the transition metal catalyst.

12. The hydroformylation process as set forth in claim 8, wherein the monodentate phosphine ligand is one or more selected from the group consisting of tri-m-tolylphosphine (TMTP), diphenyl(p-tolyl)phosphine(DPPTP), tris(2,6-dimethoxyphenyl)phosphine(TDMPP), tris(4-methoxyphenyl)phosphine(TMPP), trimesitylphosphine(TMSTP), tris-3,5-xylylphosphine(TXP), tricyclohexylphosphine(TCHP), tribenzylphosphine(TBP), benzyl diphenylphosphine (BDPP), and diphenyl-n-propylphosphine(DPMPP).

13. The hydroformylation process as set forth in claim 8, wherein the monodentate phosphine oxide ligand is one or more selected from the group consisting of tri-m-tolylphosphine oxide(TMTIO), diphenyl(p-tolyl)phosphine oxide (DPPTPO), tris(2,6-dimethoxyphenyl)phosphine oxide(TDMPPO), tris(4-methoxyphenyl)phosphine oxide (TMPPO), trimesitylphosphine oxide(TMSTPO), tris-3,5-xylylphosphine oxide(TXPO), tricyclohexylphosphine oxide (TCHPO), tribenzylphosphine oxide(TBPO), benzyl diphenylphosphine oxide(BDPPO), and diphenyl-n-propylphosphine oxide(DPMPPO).

14. The hydroformylation process as set forth in claim 8, wherein the olefin-based compound is a compound that is represented by the following Formula 5

[Formula 5]

wherein $R_7$ and $R_8$ are each independently any one selected from the group consisting of hydrogen, an alkyl group having 1 to 20 carbon atoms, a fluorine group(—F), a chlorine group (—Cl), a bromine group(—Br), a trifluoromethyl group(—$CF_3$), and an aryl group having 0 to 5 substituent groups and 6 to 20 carbon atoms, and the substituent group is nitro(—$NO_2$), fluorine(—F), chlorine(—Cl), bromine(—Br), a methyl group, an ethyl group, a propyl group, or a butyl group when the aryl group is substituted.

15. The hydroformylation process as set forth in claim 8, wherein the olefin-based compound is one or more compounds selected from the group consisting of ethene, propene, 1-butene; 1-pentene, 1-hexene, 1-octene, and styrene.

16. The hydroformylation process as set forth in claim 8, wherein the solvent is one or more compounds selected from the group consisting of propanaldehyde, butylaldehyde, pentylaldehyde, valeraldehyde, acetone, methyl ethyl ketone, methyl isobutyl ketone, acetophenone, cyclohexanone, ethanol, pentanol, octanol, texanol, benzene, toluene, xylene, orthodichlorobenzene, tetrahydrofuran, dimethoxyethane, dioxane, methylene chloride, and heptane.

17. The hydroformylation process as set forth in claim 8, wherein a molar ratio of CO:$H_2$ of the synthesis gas is in the range of 5:95 to 70:30.

18. The hydroformylation process as set forth in claim 8, wherein the hydroformylation reaction is performed at a temperature in the range of 20 to 180° C.

19. The hydroformylation process as set forth in claim 8, wherein the hydroformylation reaction is performed at a pressure in the range of 1 to 700 bar.

* * * * *